United States Patent
Borth et al.

(10) Patent No.: US 10,264,776 B2
(45) Date of Patent: *Apr. 23, 2019

(54) BEDBUG DETECTION, MONITORING AND CONTROL TECHNIQUES

(71) Applicant: Dow AgroSciences, LLC, Indianapolis, IN (US)

(72) Inventors: Paul W. Borth, Zionsville, IN (US); Nailah Orr, Carmel, IN (US); Peter N. Scherer, Lebanon, IN (US); Brian M. Schneider, Carmel, IN (US); Mike P. Tolley, Indianapolis, IN (US); Christopher J. Voglewede, Lafayette, IN (US); Gary D. Crouse, Noblesville, IN (US); David G. McCaskill, Greenwood, IN (US); Kerrm Y. Yau, Carmel, IN (US); Edward L. Olberding, Zionsville, IN (US); Joseph J. DeMark, Westfield, IN (US); Marc L. Fisher, Blacksburg, VA (US)

(73) Assignee: Dow AgroSciences LLC, Indianapolis, IN (US)

( * ) Notice: Subject to any disclaimer, the term of this patent is extended or adjusted under 35 U.S.C. 154(b) by 405 days.

This patent is subject to a terminal disclaimer.

(21) Appl. No.: 14/594,613

(22) Filed: Jan. 12, 2015

(65) Prior Publication Data

US 2015/0121745 A1 May 7, 2015

Related U.S. Application Data

(60) Continuation of application No. 14/153,723, filed on Jan. 13, 2014, now Pat. No. 8,984,804, which is a
(Continued)

(51) Int. Cl.
*A01M 1/02* (2006.01)
*G01N 33/68* (2006.01)
(Continued)

(52) U.S. Cl.
CPC ............ *A01M 1/2011* (2013.01); *A01M 1/02* (2013.01); *A01M 1/103* (2013.01);
(Continued)

(58) Field of Classification Search
CPC .... A01M 1/2011; A01M 1/2005; A01M 1/20; A01M 1/00; G01N 33/68; G01N 33/50;
(Continued)

(56) References Cited

U.S. PATENT DOCUMENTS

| 1,962,420 A | 6/1934 | Bradley |
| 4,157,629 A | 6/1979 | Parks |

(Continued)

FOREIGN PATENT DOCUMENTS

| KR | 10-2004-13761 | * | 3/2005 | ............ A01M 1/145 |
| WO | 99/17139 | | 4/1999 | |

(Continued)

OTHER PUBLICATIONS

European Communication pursuant to Article 94(3) EPC; European Application No. 07852871.8-1405, dated Sep. 30, 2013, 4 pages.
(Continued)

*Primary Examiner* — Christine T Mui
(74) *Attorney, Agent, or Firm* — Barnes & Thornburg LLP

(57) ABSTRACT

One nonlimiting variation of a detection arrangement includes one or more sensors each structured to detect at least one biochemical substance indicative of biochemistry of one or more target insect species and provide a corresponding sensor signal, a controller responsive to the sensor signal of each of the one or more sensors to determine if the one or more insect species are present and generate a corresponding output signal, and an indicator responsive to the output signal to indicate the presence of the one or more insect species.

15 Claims, 7 Drawing Sheets

Related U.S. Application Data continuation of application No. 13/723,760, filed on Dec. 21, 2012, now Pat. No. 8,661,728, which is a continuation of application No. 12/968,620, filed on Dec. 15, 2010, now Pat. No. 8,375,626, which is a continuation of application No. 12/800,462, filed on May 14, 2010, now Pat. No. 7,905,048, which is a division of application No. 11/975,914, filed on Oct. 22, 2007, now Pat. No. 7,743,552.

(60) Provisional application No. 60/854,378, filed on Oct. 25, 2006, provisional application No. 60/853,573, filed on Oct. 23, 2006.

(51) Int. Cl.
  *A01M 1/20*    (2006.01)
  *G08B 21/18*   (2006.01)
  *A01M 1/10*    (2006.01)
  *G01N 33/48*   (2006.01)

(52) U.S. Cl.
  CPC ........... *A01M 1/2022* (2013.01); *G01N 33/68* (2013.01); *G08B 21/18* (2013.01); *Y10S 436/815* (2013.01)

(58) Field of Classification Search
  CPC ...... G01N 33/48; G01N 33/00; Y10T 436/12; Y10T 436/11; Y10T 436/00; Y10S 436/815; Y10S 436/00
  USPC ....... 436/131, 127; 43/131, 132.1, 112, 113, 43/114
  See application file for complete search history.

(56) References Cited

U.S. PATENT DOCUMENTS

| | | | |
|---|---|---|---|
| 4,212,129 | A | 7/1980 | Shumate |
| 4,843,752 | A | 7/1989 | Munemasa et al. |
| 4,873,786 | A | 10/1989 | Franco |
| 4,951,414 | A | 8/1990 | Mewissen |
| 4,967,283 | A | 10/1990 | Forbes |
| 5,042,194 | A | 8/1991 | Cohen |
| 5,044,112 | A | 9/1991 | Williams |
| 5,118,610 | A | 6/1992 | Kitto et al. |
| 5,142,129 | A | 8/1992 | Nakamura et al. |
| 6,002,817 | A | 12/1999 | Kopelman et al. |
| 6,255,652 | B1 | 7/2001 | Moyer |
| 6,404,210 | B1 | 6/2002 | Su |
| 6,445,301 | B1 * | 9/2002 | Farrell ................ A01M 31/002 340/384.2 |
| 6,478,440 | B1 | 11/2002 | Jaworski et al. |
| 6,568,123 | B2 | 5/2003 | Nelson et al. |
| 6,937,156 | B2 | 8/2005 | Gardner, Jr. et al. |
| 7,743,552 | B2 | 6/2010 | Borth et al. |
| 7,905,048 | B2 | 3/2011 | Borth et al. |
| 8,375,626 | B2 | 2/2013 | Borth et al. |
| 8,661,728 | B2 | 3/2014 | Borth et al. |
| 2001/0033230 | A1 | 10/2001 | Barber et al. |
| 2003/0184442 | A1 | 10/2003 | Gardner, Jr. et al. |
| 2004/0200129 | A1 | 10/2004 | Studer et al. |
| 2005/0091911 | A1 | 5/2005 | Matts et al. |
| 2006/0150472 | A1 | 7/2006 | Harris |
| 2007/0044372 | A1 | 3/2007 | Lang et al. |
| 2007/0169401 | A1 * | 7/2007 | Chyun .................. A01M 1/145 43/113 |
| 2008/0148624 | A1 | 6/2008 | Borth et al. |
| 2009/0100743 | A1 | 4/2009 | Prater |
| 2010/0223839 | A1 | 9/2010 | Garcia-Perez et al. |

FOREIGN PATENT DOCUMENTS

| | | |
|---|---|---|
| WO | 2007/014344 A2 | 2/2007 |
| WO | 2008/051501 | 5/2008 |

OTHER PUBLICATIONS

European Search Report, European Application No. 07852871, dated Jun. 23, 2010, 7 pages.
Australian Patent Examination Report No. 1, Australian Patent Application No. 2013200548, dated Sep. 16, 2013, 3 pages.
Hale, J.E., Butler, J.P., Gelfanova V., You, J. and Knierman, M.D. (2004) A Simplified procedure for the reduction of alkylation of cysteine residues in proteins prior to proteolytic digestion and mass epotral analysis. Anal. Biochem. 333:174-181 (2004).
Link, A.J., Eng J., Schieltz, D.M., Carmack, E., Mize G.J., Marris, D.R., Garvick, B.M., Yates J.R. (1999) Direct analysis of protein complexes using mass spectrometry. Nature Biotechnol. 17:676-682 (1999).
Valenzuala, J.G., Charlab, R., Galperin, M.Y., Ribeiro, J.M. (1998) Purification, cloning, and expression of an apyrase from the bed bug Cimex lectularius. A new type of nucleotide-binding enzyme. J. Biol. Chem., vol. 273, No. 46, pp. 30583-30590 (1998).
Valenzuela, J.G., Ribeiro, J.M. (1998) Purification and cloning of the salivary nitrophorin from the hemipteran Cimex lectularius. J. Exp. bio. 201:2659-2664 (1998).
Valenzuela, J.G., High-through put approaches to study salivary proteins and genes from vectors of disease, Insect Biochemistry and Molecular Biology (Oct. 2002) vol. 32, pp. 1199-1209.
Collins, R.P., Carbonyl Compounds Produced by the Bedbug, Cimex Lectularius, Ann. Entomol. Soc. Am (61, No. 5, 1138-40, 1968).
Leverkus, M., Jochim, R.C., Shad, S. Brocker, E.B., Andersen, J.F., Valenzuala, J.G., Trautmann, A., Bullous Allergic Hypersensitivity to Bed Bug Bites Medicated by IgE against Salivary Nitrophorin, Journal of Investigative Dermatology (2006), 126, 91-96.
Valenzuela et al. A Salivary Nitrophorin (Nitric-Oxide-Carrying Hemoprotein in the Bedbug Cimex Lectularius, the Journal of Experimental Biology, Mar. 1995, 1519-1526, 198, The Company of Biologists, Great Britain.
European Search Report, European Application No. 14164104.3-1405, dated Aug. 19, 2014, 7 pages.

* cited by examiner

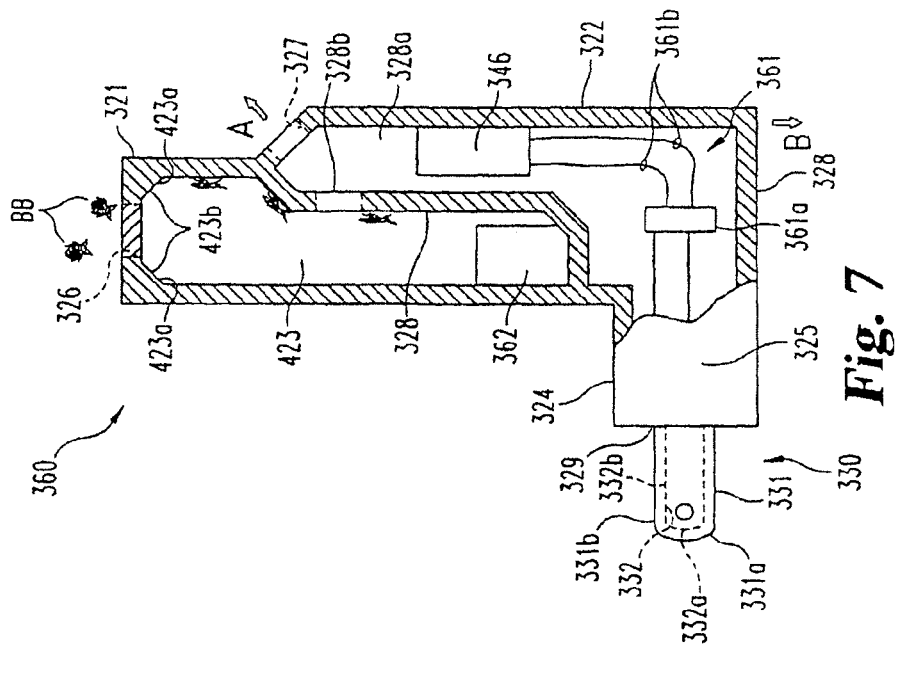
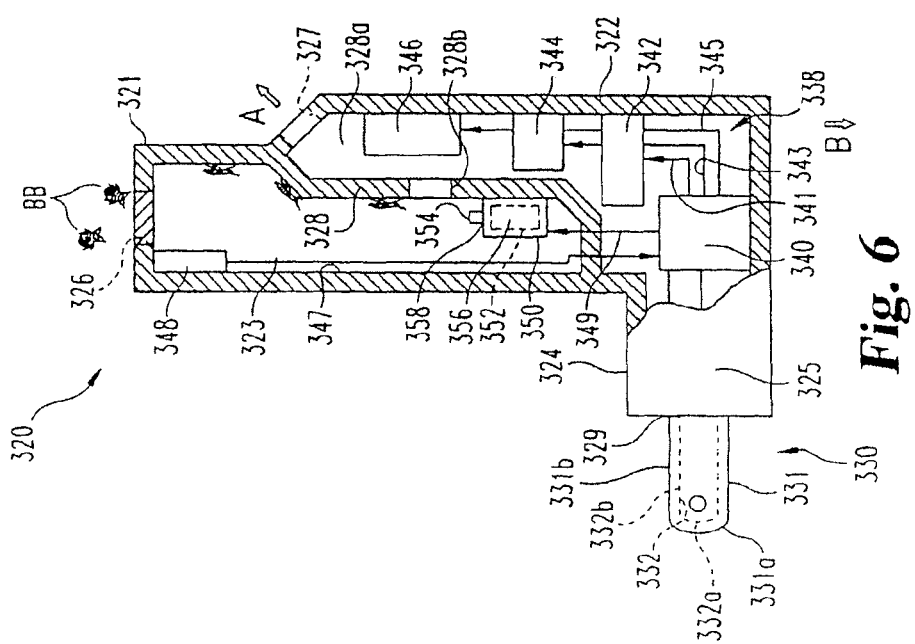

BEDBUG DETECTION, MONITORING AND CONTROL TECHNIQUES

CROSS-REFERENCE TO RELATED APPLICATIONS

The present application is a continuation of and claims priority to U.S. patent application 14/153,723 filed on Jan. 13, 2014, now U.S. Pat. No. 8,984,804, which is a continuation of U.S. patent application Ser. No. 13/723,760 filed on Dec. 21, 2012, now U.S. Pat. No. 8,661,728, which is a continuation of U.S. patent application Ser. No. 12/968,620 filed on Dec. 15, 2010, now U.S. Pat. No. 8,375,626, which is a continuation of U.S. patent application Ser. No. 12/800,462 filed on May 14, 2010, now U.S. Pat. No. 7,905,048, which is a divisional of U.S. patent application Ser. No. 11/975,914 filed on Oct. 22, 2007, now U.S. Pat. No. 7,743,552, which claims priority to U.S. Provisional Patent Application No. 60/853,573 filed Oct. 23, 2006 and to U.S. Provisional Patent Application No. 60/854,378 filed Oct. 25, 2006, each of which is incorporated herein by reference in its entirety.

BACKGROUND

The present invention relates to pest control, and more particularly, but not exclusively, relates to the detection, monitoring, and control of insects, including for example, bedbugs.

Recent data suggests bedbug infestations (*Cimex* species) of human domiciles are on the rise. At least 92 species have been identified globally, of which at least 16 species are in the North American continent. Generally, bedbugs are parasitic pests with its hosts including humans and various domesticated animals. It is believed that bedbug infestations are becoming more problematic now at least in part because long acting, residual insecticides are no longer being used to keep bedbug populations in check. In addition, increased international travel and insecticide resistance have made bedbug infestations spread and control with insecticides very difficult. In terms of scale, such infestations are of particular concern for hoteliers, cruise ships, trains, daycare facilities, and the like because of the business reputation risk posed by bad press or bad reviews. Other problematic areas tend to include nursing homes, barracks, dorms, hospitals, and various other forms of high density housing. Nonetheless, single family homes can likewise be impacted adversely.

For many of these dwellings, the pervasive application of long acting insecticides by spraying and/or dusting is undesirable. As a result, new approaches to bedbug detection, monitoring, and control are being sought. The present application provides contributions along these lines that are not only applicable to bedbugs, but may also find application in the detection, monitoring and control of other species of insects.

SUMMARY

One embodiment of the present application includes a unique technique to detect, monitor and/or control insect infestations. Other embodiments include unique methods, systems, devices, and apparatus to detect, monitor and/or control bedbugs.

A further embodiment includes: a detection arrangement including one or more sensors each structured to at least detect nitrophorin and provide a corresponding sensor signal; a controller responsive to the sensor signal of each of the one or more sensors to determine if the nitrophorin is indicative of bedbug presence and generate a corresponding output signal; and an indicator responsive to the output signal to indicate the presence of the bedbugs.

Still a further embodiment comprises: operating an insect control or detection device to determine if bedbugs are present in a room that includes analyzing a substance from the room to detect nitrophorin and indicating that bedbugs are present to an operator if nitrophorin is detected by the analyzing of the substance.

Yet a further embodiment for determining the presence of bedbugs in a room comprises obtaining a sample of a substance from the room; analyzing the sample to determine if nitrophorin is present in the substance; and providing an indication of the presence of bedbugs in response to the determination of the presence of nitrophorin.

Accordingly, one object of the present invention is to provide a unique technique to control insect infestation.

Another object is to provide a unique method, system, device, or apparatus to control or detect and monitor for bedbugs.

Further embodiments, forms, features, aspects, benefits, and advantages of the present application shall become apparent from the description and figures provided herewith.

BRIEF DESCRIPTION OF THE DRAWING

FIG. 6 is a diagrammatic, partial sectional view of a first type of device of the system of FIG. 5 that includes an insecticide to eliminate bedbugs.

FIG. 7 is a diagrammatic partial sectional view of a second type of device of the system of FIG. 5. This second type of device can be used in addition to or in lieu of the device of FIG. 6.

DETAILED DESCRIPTION OF REPRESENTATIVE EMBODIMENTS

Figure 1:
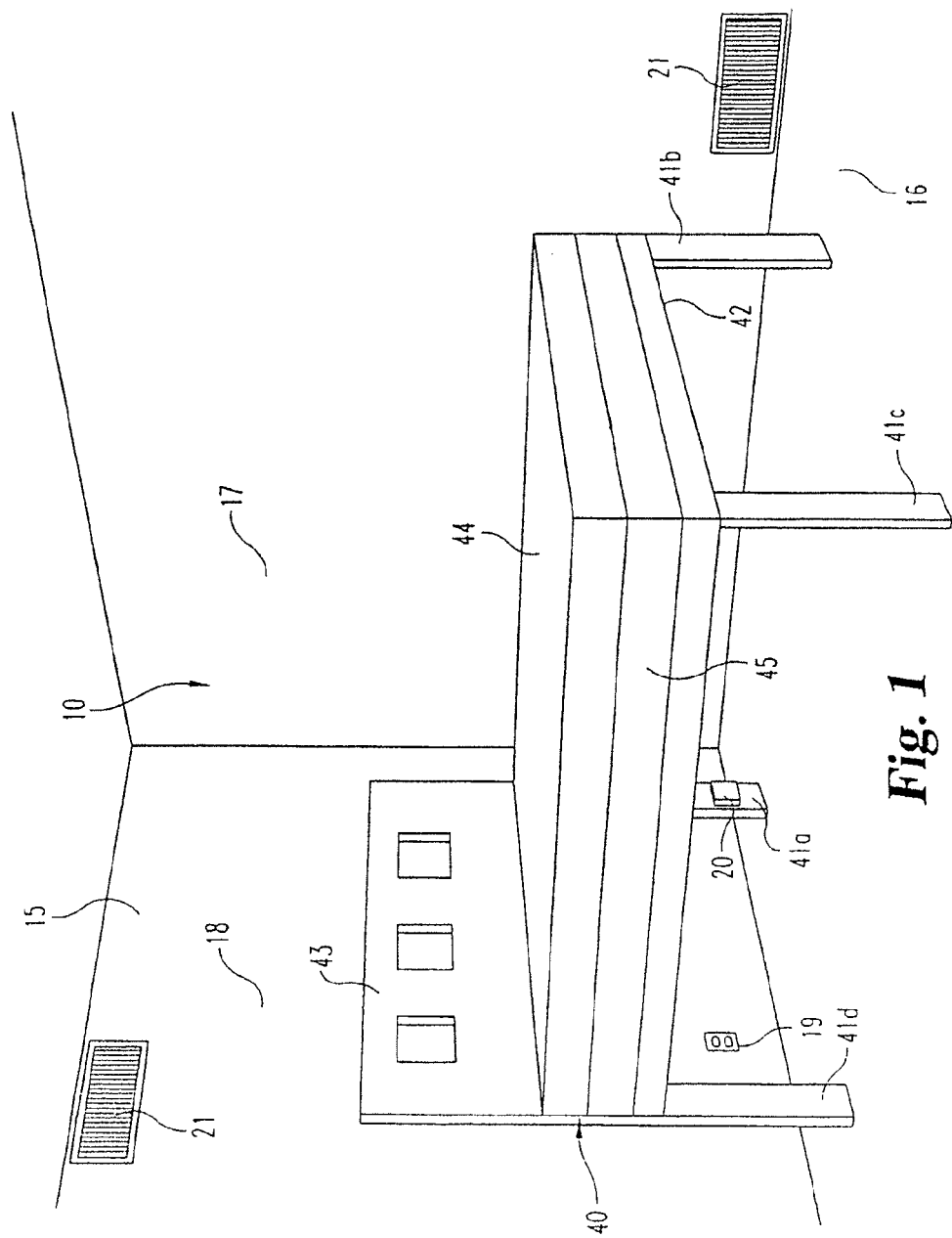
FIG. 1 is a diagrammatic view of a system suitable to detect and address bedbug infestation.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring now to FIG. 1, there is illustrated a diagrammatic view of a system 10 suitable to address an insect infestation, such as bedbugs, in room 15. System 10 includes at least one device 20, which, as illustrated, is attached to leg 41a of bed 40 and is suitable for one or more of detecting, monitoring and controlling an insect population, such as a bedbug population. The total number of devices 20 used in system 10 may vary in relation to the infestation problem and/or the time period in which an effective removal is desired. Bed 40 further includes legs 41b-41d which are interconnected via a frame 42 and a headboard 43 to form a support for a mattress 44 placed on top of box springs 45. It should be appreciated that in alternative embodiments, bed system 40 may comprise one or more components in addition to or in lieu of those illustrated in FIG. 1. For example, in other embodiments bed system 40 may lack box springs 45 or headboard 43, or may include a footboard. In yet another embodiment, bed system 40 may only include mattress 44 on top of box springs 45 set directly on floor 16 of room 15. Device 20 may be attached to bed leg 41a by any type of fastener, including but not limited to, a nail, screw, bolt, tack, clamp, strap, adhesive, tape, hook and loop connector (such as VELCRO), and/or such different fastener variety as would occur to those skilled in the art. In an alternative embodiment not illustrated, device 20 may be placed elsewhere on the structure of bed system 40. For example, device 20 may be placed on any of legs 41a-41d, frame 42, headboard 43, a portion of mattress 44, or on box springs 45. In another alternative embodiment, device 20 may be placed on either of wall 17 or 18, or elsewhere in the room 15.

It should be understood that as illustrated in FIG. 1, system 10 is being used in room 15, where room 15 belongs to a: dormitory, hostel, shelter, hotel, motel, bed and breakfast, inn, tent, cabin, nursing home, hospital, and/or house, just to name a few possibilities. In a further embodiment, system 10 may be used at any location in which a blood meal, particularly a human blood meal, might be in the presence of a bedbug during a bedbug feeding period, such as nighttime. For example, system 10 might be placed in the sleeping rooms or cabins of a vehicle (such as a ship, train, or motor coach), or in sleeping rooms of daycare centers and schools. System 10 may be individually configured in accordance with the specific attributes of each location.

Additionally, the placement of device 20 within a designated area may not only vary with different locations, but can also vary in accordance to visual evidence indicating the increased probability of nearby bedbugs or bedbug harborages. For example, device 20 may be placed in close proximity to one or more of bedbug excrement or fecal matter, molted exoskeleton shells, eggs, or blood spots. In one embodiment, device 20 may be placed in close proximity to the likely location of a human blood meal host, like for example near mattress 44. In another embodiment not illustrated, device 20 may be placed on or near one or more bedbug harborages in the form of a crack, gap, or crevice. For example, device 20 may be placed near peeling wallpaper or cracks in the drywall or plaster of either of walls 17 and 18 in room 15. Additionally, for an embodiment in which room 15 includes one or more trim moldings mounted to walls 17 and/or 18, device 20 may be placed in close proximity thereto. For one variation, device 20 is shaped and structured to simulate trim molding or another common decor feature typically found in a bedroom. In another embodiment, device 20 may be placed next to flooring on the surface of floor 16, like for example near the edge of either securely fastened or rolled back carpet. In another variation, device 20 may be placed on or near one or more of air duct vents 21, which may communicate with one or more of a supply air duct or a return air duct, as would be appreciated by one having skill in the art. In another form, device 20 may be placed in the supply air duct or return air duct communicating via vents 21. It is further contemplated that device 20 may be placed in any position effective for bedbug control.

Figure 2:
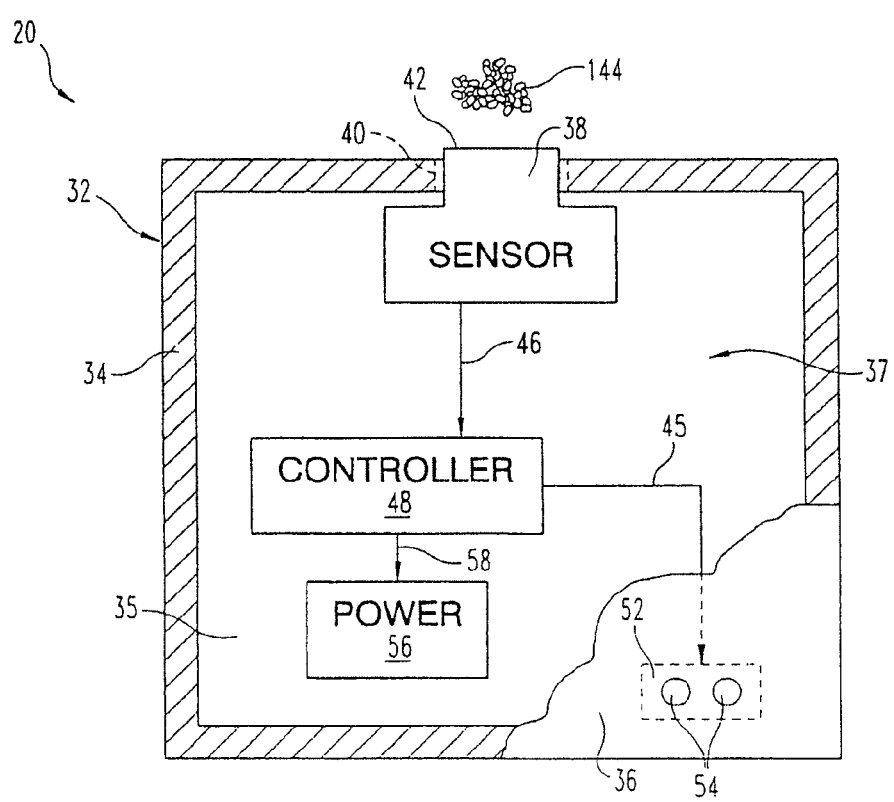
FIG. 2 is a diagrammatic, partial sectional view of a first type of device of the system of FIG. 1.

Device 20 is shown in greater detail in a diagrammatic partial sectional view in FIG. 2. Device 20 includes a housing member 32 defined by an exterior wall 34 and a top cover 36 enclosing an internal chamber 35 which houses a sensing arrangement 37 generally including interconnected sensor 38, controller 48, indicator 52, and power source 56. It is contemplated that in alternative embodiments not shown, sensing arrangement 37 may include one or more components in addition to or in lieu of that illustrated in FIG. 2. It should further be understood that in various embodiments the componentry of sensing arrangement 37 may be arranged in one or more alternative fashions to that depicted in FIG. 2.

Sensor 38 extends through exterior wall 34 at opening 40 such that sensing portion 42 may be externally exposed to the environment of the area in which device 20 is placed. Sensor 38 is generally structured to analyze one or more biochemical substances 144 to determine if it is indicative of bedbug biochemistry. A few detailed examples of the biochemical detection mechanisms performed with sensor 38 are further described hereinafter in connection with reference to FIGS. 1-3 generally. While sensing portion 42 is illustrated as being at least partially external to chamber 35, it should be understood that in alternative embodiments sensing portion 42 may be entirely disposed within chamber 35. In these embodiments, device 20 may include one or more components to convey a biochemical substance. For example, with regard to such substance 144 being carried in the air, an air handling system like a fan or suction device can be included to at least bring part of a biochemical substance 144 into internal chamber 35 through opening 40 to engage sensing portion 42 of sensor 38. In another form, device 20 may include one or more openings in addition to opening 40, with each additional opening being structured to guide a medium carrying biochemical substance 144 into contact with an internally disposed sensing portion 42. For example, when device 20 is placed on or near air duct vents 21, or in the air ducts themselves, the opening may be structured to channel the airflow moving around device 20 into contact with sensing portion 42.

In response to biochemical substance 144, sensor 38 generates a corresponding sensor signal that is conveyed along signal pathway 46 to controller 48. Controller 48 operates in accordance with operating logic to determine if the signal indicates the presence of biochemistry indicative of bedbug presence and/or another target insect type. Controller 48 is comprised of one or more components that may be configured as a single unit, or distributed among two or more units. Such components may be of a solid state, electromagnetic, optical, and/or different variety as would occur to those skilled in the art. The controller 48 may include analog circuitry, digital circuitry, and/or a hybrid combination of both of these types. In one form, the controller 48 is of the programmable variety that executes algorithms and processes data in accordance with its operating logic being defined by programming instructions (such as software or firmware) Alternatively or additionally, the operating logic for controller 48 is at least partially defined by hardwired logic or other hardware.

After controller 48 receives and processes the sensor signal, a controller output signal is output along signal pathway 45 to an indicator 52. Indicator 52 is generally structured to provide a human operator with an output to indicate the presence or absence of a biochemical substance 144 indicative of bedbug biochemistry. As illustrated in FIG. 2, indicator 52 includes an output in the form of visual markers 54. Visual markers 54 may be in one or more forms of a light, such as a light emitting diode (LED), fluorescent, incandescent, and/or neon type, amongst other possibilities. In each form, the presence of biochemical substance 144 may be indicated by, for example, a discrete yes/no indicator, a color change, a flashing sequence, or other change in indicator state. In alternative forms, indicator 52 may provide an output indicating the presence of biochemical substances 144 in the form of a colorimetric strip or an aural/audio signal. In one form, when the output of indicator 52 is in an aural form, the presence of biochemical substance 144 may be indicated by one or more of a single or sequential beep, chime, ring, horn, and click, just to name a few possibilities. In one implementation, a quantitative evaluation is provided by varying the indication with the number of bedbugs present, such as providing a more intense color indicator, a louder and/or more frequent aural indicator, or the like in response to detection of a greater bedbug presence.

As illustrated in FIG. 2, sensing arrangement 37 includes a power supply 56 structured to send electrical power to controller 48, sensor 38, and/or indicator 52, as needed. Only power supply pathway 58 to controller 48 is illustrated. It should be appreciated that certain types of sensor 38 and/or indicator 52 may derive any needed electrical power from pathway 46 and/or 58 as needed, and that in still other embodiments such components are passive, not needing any type of persistent electrical power source.

As illustrated, power supply 56 is located within internal chamber 35 and may be provided for example, in the form of one or more electrochemical cells or battery of such cells. In an alternative embodiment, power is sourced externally from an electrical socket, such as wall receptacle 19 in FIG. 1, in which case, supply 56 is understood to be at least partially external to device 20. It should be appreciated that sensing arrangement 37 may be modified for use with a DC power source or an AC power source and that the modification of components may be dependent upon the availability of one or more forms of the power source. In another form, a renewable external power source, such as a solar cell disposed on top cover 36 of device 20, may be used to provide sensing arrangement 37 with power. It is further contemplated that in other embodiments one or more of sensor 38, controller 48, and indicator 52, each includes its own power source. The components of sensing arrangement 37 including sensor 38, controller 48, and indicator 52 may be alternatively interconnected. For example, in one arrangement the components of sensing arrangement 37 may be interconnected using wired or wireless techniques with corresponding signals structured in an appropriate fashion. It should be appreciated that some implementations may be passive in nature, so that no power source is needed, and alternatively or additionally no controller may be utilized. As further described elsewhere in the present application, a colorimetric strip sensitive to one or more bedbug-specific biochemicals provides one nonlimiting example of a sensor/indicator device that lacks a power source and controller.

Figure 3:
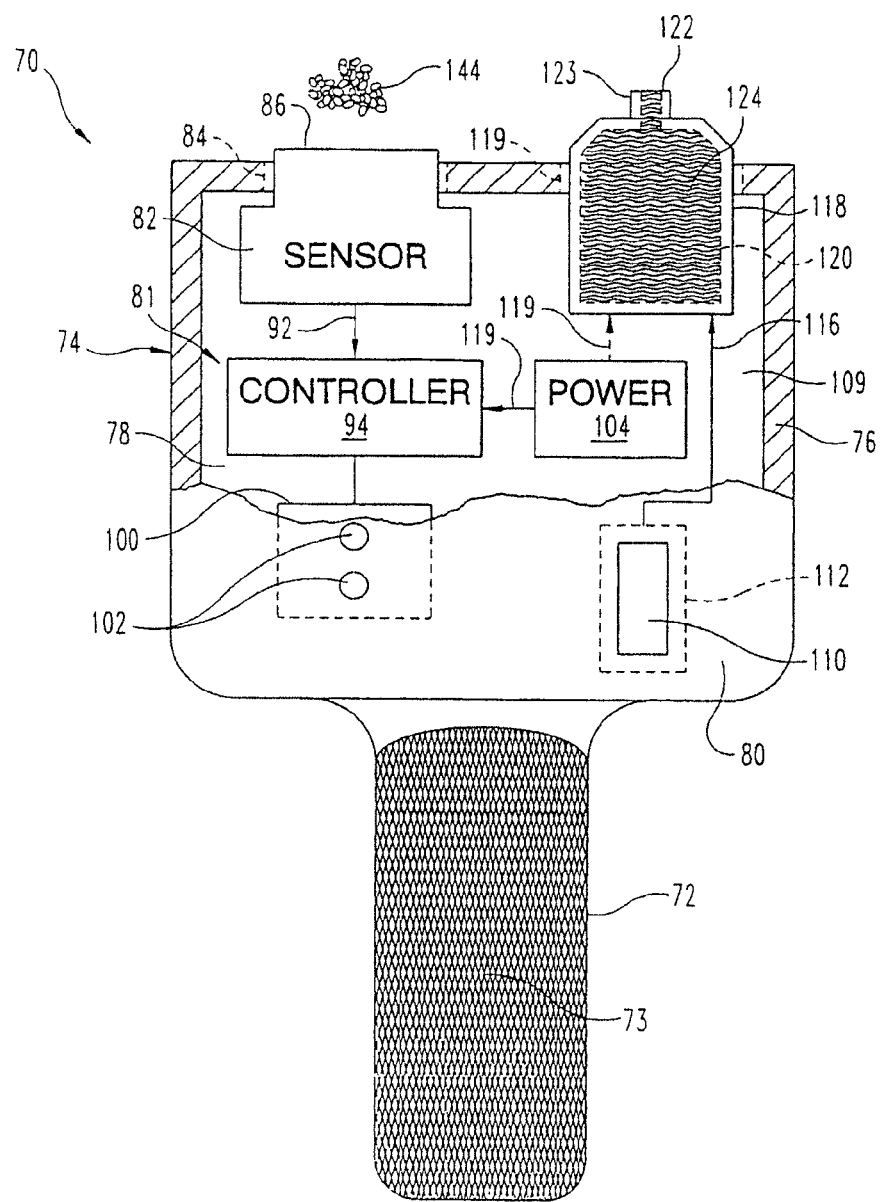
FIG. 3 is a diagrammatic partial sectional view of a second type of device of the system of FIG. 1 that eliminates bedbugs with an insecticide. This second type of device can be used in addition to or in lieu of the device of FIG. 2.

Once bedbugs have been detected, an operator can determine whether to conduct an extermination process, such as the application of one or more types of insecticides toxic to bedbugs. Such types of insecticides are further described with reference to FIG. 3 as follows. FIG. 3 depicts a diagrammatic partial sectional view of device 70 which is suitable for use in system 10 and configured for one or more of detecting, monitoring and controlling an insect population, such as a bedbug population. Device 70 includes an operator handle 72 opposite a housing member 74. Operator handle 72 is generally structured for engagement by the hand of a human operator and may including knurling 73 to increase operator gripping capabilities. In alternative forms not shown, operator handle 72 may include one or more grip enhancing features in addition to or in lieu of knurling 73. For example, in one form a rubber coating may be applied to operator handle 72 while in another form operator handle 72 may include one or more ergonomic hand grips. In another embodiment, handle 72 may be free from any grip enhancing features.

Housing member 74 includes an exterior wall 76 and a top cover 80 which together form an internal chamber 78 structured to house and provide protection for sensing arrangement 81 and exterminating arrangement 109. Sensing arrangement 81 includes an interconnected sensor 82, controller 94, indicator 100, and power source 104. It is contemplated that in alternative embodiments not shown, sensing arrangement 81 may include components in addition to or in lieu of that illustrated in FIG. 3. It should further be understood that in various embodiments the componentry of sensing arrangement 81 may be arranged in one or more alternative fashions to that depicted in FIG. 3.

Sensor 82 extends through exterior wall 76 at opening 84 such that sensing portion 86 may be externally exposed to the environment of the area in which device 70 is being used. Similar to sensor 38, sensor 82 is generally structured to analyze one or more biochemical substances 144 indicative of bedbug presence. A few detailed examples of the biochemical detection mechanisms performed with sensor 82 are further described hereinafter in connection with reference to FIGS. 1-3 generally. While sensing portion 86 is illustrated as extending beyond internal chamber 78—being at least partially external thereto—it should be understood that in alternative embodiments sensing portion 86 may be entirely disposed within chamber 78. In these embodiments, as described above, device 70 may include one or more structures to convey biochemical substances 144, bringing all or part of it into contact with an internally disposed sensing portion 86. Device 70 may also include one or more openings in addition to opening 84, with each additional opening being structured to guide a medium carrying biochemical substance 144 into contact with an internally disposed sensing portion 86.

Upon sensing biochemical substances 144 indicative of bedbug biochemistry, sensor 86 sends a corresponding sensor signal to controller 94 via signal pathway 92. Controller 94 can be configured in any of a number of ways such as described in connection with controller 48. After controller 94 receives and processes sensor signal 90, a controller output signal is sent to indicator 100 via signal pathway 96. Indicator 100 is structured to provide a human operator with an output signal notifying the operator of the presence of biochemical substance 144 indicative of bedbug biochemistry. Indicator 100 includes visual markers 102 to notify a human operator of bedbug biochemistry similarities and the probability of the presence of one or more bedbugs. Visual markers 102 are generally structured and operative in a manner similar to that described above in regard to visual markers 54. Furthermore, as indicated above, indicator 100 may provide output to notify a human operator of the presence of biochemical substance 144 indicative of a bedbug in one or more forms in addition to or in lieu of visual markers 102. For example, an aural signal or a colorimetric strip may be utilized. It should be appreciated that any output signals provided by indicator 100 may include any one or more features described above with respect to the output signals which may be provided by indicator 52.

A power source 104 is included in internal chamber 78 that provides electric power to controller 94, sensing arrangement 81, and exterminating arrangement 109, respectively. The provision of such power to arrangement 81 and/or 109 may be via controller 94 and/or by separate power conveying pathways not shown. In still other embodiments, some or all of the components of arrangements 81 and 109 are passive in nature, not requiring a persistent source of power. Power source 104 may be in the form of a DC battery, or in an alternative form, may not be positioned within internal chamber 78. In one such alternative, the power source 104 may be an AC source, such as wall receptacle 19 in FIG. 1. As described above in regard to arrangement 37, it is contemplated that the components of arrangements 81, 109 may be individually powered and can be interconnected through one or more wired or wireless pathways.

When sensing arrangement 81 indicates one or more biochemical substances 144 of bedbugs, a human operator may use device 70 to commence extermination via exterminating arrangement 109. Exterminating arrangement 109 includes a pushbutton 110. In response to the depression of pushbutton 110, control module 112 sends a release signal on signal pathway 116 to an exterminating module 118. As illustrated in phantom, exterminating module 118 includes an internal reservoir 120 communicating with an applicator tip 122. A closing member 123 is biased to a closed position adjacent the applicator tip 122. The contents of reservoir 120 include an insecticide 124 toxic to bedbugs. In response to the release signal from signal pathway 116, member 123 opens to release insecticide 124 in a fluid form, such as an aerosol, gas, liquid, or powder. When the operator releases the depressed button 110, the release signal changes state in such manner that member 123 returns to its closed state in response, ceasing the release of insecticide 124.

In an alternative embodiment not shown, exterminating module 118 may be directly connected to controller 94 and may react directly to the presence of biochemical substance 144 to release insecticide 124 automatically, without any action by a human operator. In one such form, insecticide 124 is control released and confined to the area in which biochemical substance 144 is detected. In another embodiment exterminating system 109 may be mechanical in nature, such that as operator release button 110 is depressed, member 123 is opened to permit release of insecticide 124. In this form, exterminating system 109 may not include any connection to sensing arrangement 81 or power source 104. Insecticide 124, non-limiting examples of which will be provided herein below, may be of one or more forms effective for exterminating a bedbug population as would be appreciated by one having ordinary skill in the art. The insecticide can be provided in a form intended to be ingested by bedbugs and/or to provide exposure sufficient for extermination by external contact with the body of a bedbug. In still another form, the insecticide may be provided in a vapor form which may be insufflated through one or more spiracles of a bedbug.

Referring now generally to FIGS. 1-3, devices 20, 70 may comprise any number of suitable materials including certain polymers, woods, metals, or any mixtures thereof. Moreover, one or more of devices 20 may be used with one or more of device 70 in a further embodiment. It should appreciated that each of devices 20, 70 is not limited to the form as illustrated in respective FIGS. 2 and 3. For example, device 20 may be configured for hand-held operation while device 70 may be configured for semi-permanent placement. In additional alternative forms, devices 20, 70 may be wheeled devices or robotic devices structured to scan, for example, room 15.

Indicator 52, 100 may provide information in addition to a positive or negative indication of biochemical substance 144. In one form, a relative concentration or quantitative measurement of an analyte used by sensor 38, 82 may be provided by indicator 52, 100. When such information is provided, sensor 38, 82 may include an operator viewing screen on which the relevant information is displayed. In these forms, controller 48, 94 may provide indicator 52, 100 with a pre-programmed control model upon which the human operator may compare the levels of biochemical substances 144 detected to determine if one or more bedbugs are present or if further detecting is necessary. It should also be appreciated that the output provided by indicator 52, 100 may vary in relation to a characteristic of the biochemical substance 144 analyzed by sensor 38, 86. For example, in response to different concentration levels of biochemical substance 144, indicator 52, 100 may provide visual markers 54, 102 including levels of brightness which correspond to the concentration level of biochemical substance 144. Additionally or alternatively, aural/audio signals may be provided which include volume levels and/or output sequences which correspond to the concentration level of biochemical substance 144.

In a further embodiment, information is relayed by a wired or wireless communication pathway from device 20, 70 to a remote site for further data collection and analysis. This remote site could be a computer coupled to device 20 and/or 70 by a computer network in a designated room of a hotel, nursing home, cruise ship, train, dormitory, barracks, hospital, or the like and/or could even be remote relative to such structures, like a pest control service provider business location or the like.

As indicated above, sensor 38, 82 is generally structured to analyze at least one biochemical substance 144 to determine if it is indicative of bedbug biochemistry. In addition to air handling mechanisms, transport of an analyte to sensor 38, 82 can be accomplished by a swab, wipe, tissue, or towelette or the like either with or without a wetting agent, such as distilled water, to collect a sample for biochemical analysis. Alternatively or additionally, a dust/particulate collector is utilized with or without a wetting agent. In a further approach, a liquid is applied in aerosol form to the air and/or to one or more surfaces and collected for sensor analysis. Any of these transport mechanisms can be manually and/or automatically performed. In one particular variation, the sample is collected with a device that includes an agent in liquid or aerosol form, which is intended to react with one or more biochemical indicative of bedbugs. Sensors 38, 82 can include any chemical reaction, antigen antibody reaction, galvanic, electrochemical, fluorescence, spectroscopic, and/or chromatography technique or the like to detect a biochemical substance 144 or group of such substances 144 indicative of a target insect types, such as bedbugs. Certain specific examples of these implementations are further described in the examples that follow.

It is contemplated that the biochemical substance 144 may be any compound or combination of compounds that are distinctly associated with bedbug biochemistry. In one form, biochemical substance 144 may be one or more or any combination of bedbug saliva, exoskeletons, lost antennae and other body parts, pheromones, hormones, kairomones, proteins, bodily secretions including fecal matter, other waste products or by-products, and/or seminal fluid, and eggs and egg residue. It is contemplated that arrangement 37, 81 may be modified in various embodiments to detect one or more of each the listed biochemical substances 144 as well as other biochemical substances indicative of bedbug biochemistry.

The specific biochemical substance(s) 144 analyzed may vary. In one form where the biochemical substance sought to be analyzed is a bedbug exoskeleton, chitin comprising acetylglucosamine (N-acetyl-D-glucos-2-amine) may be sensed by sensor 38, 82. In another form, when bedbug saliva is analyzed by sensor 38, 82, an anticoagulant or anesthetic may be the substance sought to be detected. In one specific implementation of saliva analysis, one or more proteins, such as nitrophorin and apyrase, or peptides forming the proteins, may be the targeted biochemical substance 144. Any one or more of mammalian red blood cells, white blood cells, platelets, glucose, iron and plasma, the plasma including but not limited to, albumin, thrombogenic factors, immunoglobulins, hormones, proteins, and/or electrolytes, may be detected as biochemical substance 144 when sensor 38, 82 analyzes bedbug fecal matter. In analyzing a substance to determine if it is bedbug seminal fluid, sensor 38, 82 may detect for the combined presence of alanine and glutamic acid and/or DNA or RNA specific to a bedbug species. In another form, sensor 38, 82 may detect the presence of bedbug hormones, kairomones, and/or pheromones in any state of matter (solid, liquid or gas). In one such implementation, sensor 38, 82 may be structured to detect for one or more of trans-oct-2-en-1-al or trans-hex-2-en-1-al. It should be appreciated that sensor 38, 82 may be structured to detect any number of combinations of compounds in order to yield a more reliable result as to the detection of a biochemical substance 144 indicative of bedbug biochemistry.

Sensor 38, 82 may include one or more features structured to facilitate chemical analysis of biochemical substance 144 to determine if it is indicative of bedbug biochemistry. In one form, sensor 38, 82 includes application of an agent as aerosol spray and/or liquid to the biochemical substance 144. Such agent is selected to cause a desired chemical reaction with the target biochemical substance(s) 144 that facilitates detection with sensor 38, 82. In one form, the agent causes an endothermic or exothermic reaction between one or more biochemical substances specific to a bedbug. In this form, sensor 38, 82 includes a thermometer structured to record differences in temperature which may result from the reaction. Upon detection of a selected amount of change in temperature, arrangement 37, 81 provides a positive indication of the presence of biochemical substance 144. In a variation of this approach, arrangement 37, 81 indicates that at least a temperature corresponding to an increased level of biochemical substance 144 is present below the threshold, at which point a human operator could decide whether to continue searching. In another form, the aerosol may be structured to provide an electrochemical reaction with the biochemical substance 144. Sensor 38, 82 may then include a meter structured to measure electrical current/voltage or other electrical property associated with the electrochemical reaction such that arrangement 37, 81 may determine if the biochemical substance 144 is indicative of bedbugs. In still other forms, the reaction results in a pH level indicative of the target biochemical(s) and/or oxygen concentration indicative of the target biochemical(s) detectable with sensor 38 and/or 82.

Sensor 38, 82 may further include a molecularly imprinted polymer structured to detect one or more potential biochemical substances 144. The molecularly imprinted polymer includes a plurality of reception sites which have been specifically modified for a targeted molecule, like for example, one of the bedbug-indicative compounds listed above. Each reception site will generally include a shape, size, and functionality unique to the targeted molecule. In one non-limiting form, the molecularly imprinted molecule may include reception sites which extract one or more of trans-oct-2-en-1-al or trans-hex-2-en-1-al from an air flow that passes thereby. Once a sufficient amount of the one or more of trans-oct-2-en-1-al or trans-hex-2-en-1-al is extracted and bound to the molecularly imprinted polymer section of sensor 38, 82, a corresponding signal to indicate bedbug presence may be sent to controller 48, 94 and/or to indicator 50, 92.

In one form in which device 20, 70 detects the presence of a bedbug exoskeleton including chitin, which comprises acetylglucosamine (N-acetyl-D-glucos-2-amine), sensor 38, 82 provides an enzyme in the form of a lysozyme. As would be appreciated by one having ordinary skill in the art, the lysozyme hydrolyzes N-acetyl-D-glucos-2-amine linkages to break-up the chitin structure. Sensor 38, 82 may be structured in one or more forms to detect the concentration of one or more molecules as the result of the hydrolysis reaction and arrangement 37, 81 may determine and indicate whether the tested sample is likely a biochemical substance 144 indicative of bedbug biochemistry based upon the concentration changes, or lack thereof, that result from the reaction.

Sensor 38, 82 may utilize one or more forms of a wipe assay in alternative embodiments. In this form, one or more wipes may be used to swab a surface desirable for analysis and then placed into an assay analyzer of sensor 38, 82. In one form, an enzyme-linked immunosorbent assay (ELISA) may be provided at sensor 38, 82 to provide detection of a targeted antibody in bedbug saliva. The assay may utilize an IgE antibody which is specific to a nitrophorin antigen present in the bedbug saliva. Another antibody coupled to an enzyme is provided which reacts with the nitrophorin-IgE antibody complex as would be appreciated by one having skill in the art. The second antibody may provide a chromogenic or fluorogenic signal indicative of the presence of the nitrophorin-IgE antibody complex. Consequently, a corresponding signal may be sent to controller 48, 94 so that arrangement 37, 81 can indicate the presence of biochemical substance 144 indicative of bedbug biochemistry.

It should be appreciated that sensor 38, 82 may utilize one or more biochemical reactions or analysis techniques to determine the presence of biochemical substance 144 indicative of a bedbug. These biochemical reactions and analysis techniques may include, but are not limited to: an electrochemical reaction; an antigen-antibody reaction; an endothermic reaction; an exothermic reaction; assay analysis; SOS-Page; a glucose reaction monitor; and Kastle-Meyer analysis just to name a few examples. Additionally or alternatively, detection based on spectrometry and/or chromatography can be utilized, including for example, mass spectrometry and liquid chromatography. Furthermore, it is contemplated that as additional biochemical substances 144 specific to bedbug biochemistry become targeted substances, arrangements 37, may be modified accordingly in order to provide adequate sensing techniques. Additionally, each of devices 20, 70 may include one or more sensors in addition to sensors 38, 82 to either provide an expanded surface area of detection or an increased number of targeted biochemicals. Furthermore, it should be appreciated that as the targeted biochemical substance 144 changes, controller 48, 94 may also change in order to adequately handle sensor signals. For example, in varying forms, controller 48, 94 may be programmed with one or more control levels upon which determination of varying targeted biochemical substance(s) 144 indicative of bedbug biochemistry is to be evaluated.

In one manner of detecting a biochemical substance 144, devices 20, 70 are specifically structured to identify the protein nitrophorin by, for example, detecting one or more peptides or peptide fragments thereof. In this form, sensor 38, 82 may be contacted with a surface in a room where bedbug infestation might be likely to facilitate potential exposure to nitrophorin. Additionally or alternatively, an exemplary sample of any substances on the surface may be obtained by a user and then exposed to sensor 38, 82. In this latter manner, it should be appreciated that the sample may be further treated or processed before exposure to sensor 38, 82, including, for example, being mixed with one or more solvents or other carrier agents as necessary to facilitate analysis by sensor 38, 82. Sensor 38, 82 may utilize any one or more of the analytical methods described above, including one or more of liquid chromatography and mass spectrometry and antigen-antibody reaction, for determining the presence of nitrophorin. If the presence of nitrophorin is positively indicated, devices 20, 70 may automatically notify a user of such. In another form, sensor 38, 82 determines the concentration of nitrophorin and compares that concentration with concentration levels pre-programmed into devices 20, 70 which are indicative of bedbug presence before notifying a user of the presence of nitrophorin. Upon the positive identification of a requisite amount of nitrophorin, a user may selectively apply an insecticide to the room or take other appropriate actions.

As an alternative or addition to biochemical sensing techniques, other bedbug sensing mechanisms can be utilized. For example, a sensor responsive to the weight of a bedbug and/or the mechanical force exerted by a bedbug may be utilized. In another instance, electromagnetic radiation is used to sense bedbugs by returning, blocking, and/or dispersing the radiation in a manner that can be detected and identified as being indicative of bedbug presence. In a specific implementation of this approach, bedbugs in device 20 and/or 70 are directed along a path such that a light beam directed across the path is broken/blocked when a bedbug travels along such path. As a result, the output signal from an optical detector responsive to the light beam changes state, indicating the presence of the bedbug. Likewise, acoustic energy, such as ultrasound, may be used to detect bedbug presence. Additionally or alternatively, tarsal recognition or spectral analysis (including without limitation ultraviolet and infrared techniques) may also be used to detect the presence of the bedbugs.

Various features of devices 20, 70 can be combined or omitted in other embodiments. In one arrangement, device 20 or 70 is provided in the form of a probe with a sensing surface defined by sensor 32, 82. For example, the sensing surface may be impregnated with a detector substance which is exposed to a liquid bearing a sample submitted for detection of insect, or bedbug, indicative biochemicals. In response to the presence of such biochemicals in the same (a positive result), the sensing surface changes color to indicate likely insect presence. As such, this surface also acts as an indicator in this arrangement, such that a separate indicator is not needed. In one form, this probe may resemble a human pregnancy test. In still other arrangements, it should be appreciated that controller, sensor, and/or indicator functions may be integral to each other such that they are represented as separate features in only a logical sense. In yet other arrangements, a controller may be absent in device 20 or 70 with sensor 38, 82 providing a signal directly to an indicator or remote data gathering/analysis site.

Figure 4:
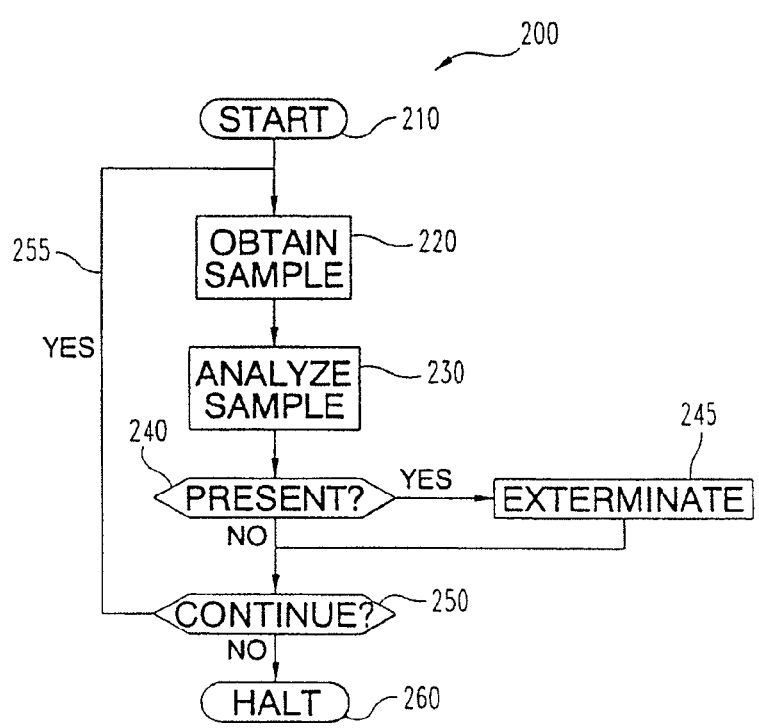
FIG. 4 is a flowchart depicting one procedure for using the system of FIG. 1.

In FIG. 4 there is depicted one procedure 200 for using system 10. At stage 210 procedure 200 is started either by attaching device 20, 70 to a desired location as indicated in FIG. 2 or by using a hand-held device as illustrated in FIG. 3. A sample of one or more substances which may potentially include one or more targeted forms of biochemical substance 144 is obtained at stage 220 to be analyzed by device 20, 70. At stage 230, sensor 38, 82 analyzes the sample to determine if it is a biochemical substance indicative of a bedbug. Sensor 38, 82 passes the analysis result onto controller 48, 94 which passes an output signal on to indicator 52, 100. Indicator 52, 100 is checked at stage 240 to determine if biochemical substance 144 is present. If biochemical substance 144 is present, then the human operator may exterminate at stage 245 using either exterminating system 109 of device 70 or an alternative extermination method as would be appreciated by one having skill in the art. At stage 250, after indicator 52, 100 indicates at stage 240 that biochemical substance 144 is not present and/or after extermination at stage 245, the human operator must determine whether to continue procedure 200. If the procedure 200 is continued, like for example at another location within the area being checked, then procedure 200 returns to restart, as indicated by arrow 255. If procedure 200 is not continued, then it halts at stage 260. Procedure 200 may be repeated continually until an entire bedbug population has been removed and/or detected or until the human operator is satisfied that a sufficient period of time has passed without any indication of bedbug presence.

In an alternative procedure, an attractant is used to lure bedbugs to a location submitted to detection with device 20 and/or 70. Such attractant can be included in device 20 or 70 and/or utilized externally/separately. These attractants can be included in a bait combined with an insecticide for ingestion by bedbugs. The attractant can include one or more naturally occurring or synthetic bedbug attracting compounds—which in one form may be structured to mimic one or more biological or physical requirements essential for bedbug survival while in another form may be known to draw bedbugs without correlation to survival—to name just a few examples. Further details regarding the characteristics of the attractant, and or combination of the attractant with a bait and/or insecticide, will be provided herein below in connection with attractant source 346 and bait 362. If used, the attractant should be selected so as not to increase the number of false positive indications of bedbug presence with sensor 32, 82 beyond an unacceptable threshold. Such circumstances may in particular arise with attractants that simulate bedbug biochemistry.

Figure 5:
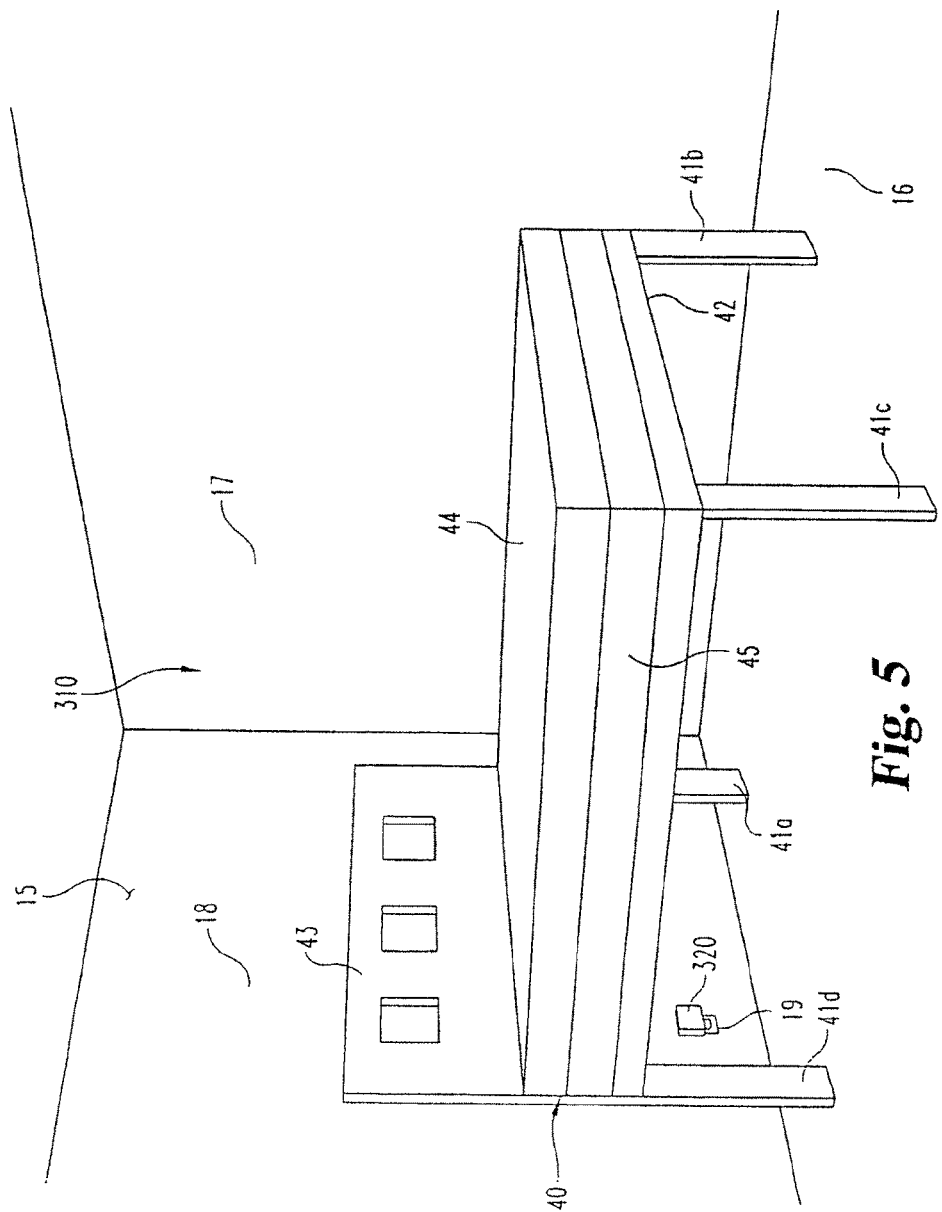
FIG. 5 is a diagrammatic view of a second type of system suitable to address bedbug infestation.

Referring now to FIG. 5, there is illustrated a diagrammatic view of a second type of system 310 suitable to address a bedbug infestation in room 15. System 310 includes at least one device 320, which, as illustrated, is engaged with electrical wall receptacle 19 of room 15 and may be suitable for one or more of detecting, monitoring and controlling a bedbug population. The total number of devices 320 used in system 310 may vary in relation to the infestation problem and/or the time period in which an effective removal is desired. While wall receptacle 19 and device 320 are located below bed system 40, it should be appreciated that in one or more forms device 320 may be placed alternatively throughout room 15. For example, in one form, device 320 may be engaged with a wall receptacle located alternatively to wall receptacle 19. In another form, device 320 may utilize a power cord to facilitate its placement on, for example, bed system 40. It should be further appreciated that, dependent on proper power supply, device 320 may generally be placed at various locations in room 15, as described above in connection with device 20.

Device 320 is shown in greater detail in a diagrammatic partial sectional view in FIG. 6. For this view, a few representative bedbugs BB are illustrated in and around device 320. Device 320 generally includes a housing member 321 including an exterior wall 322 and an outer cover 325 forming internal chambers 323 and 328a. It should be appreciated that chamber 323 is generally structured to provide a bedbug harborage for one or more bedbugs BB which may enter chamber 323 through opening 326. As illustrated, a dividing wall 328 separates chamber 323 from chamber 328a, with chamber 328a being structured to provide a channel for one more bedbug attractants to be released from chamber 328a through opening 326, which is accessible by bedbugs BB, and opening 327, which is not accessible by bedbugs BB. Opening 327 is directed to the external environment of the area in which device 320 is located, as indicated by directional arrow A. Opening 327 is generally structured to permit the attractant to be released from chamber 328a but prohibits a bedbug from entering chamber 328a so that components of operating system 338 are not disturbed. Dividing wall 328 defines one or more permeable sections or openings 328b through which attractants or heat may be dispersed from chamber 328a into chamber 323 and out of opening 326, in order to draw bedbugs BB into chamber 323; however, openings 328b are structured to prevent the passage of bedbugs BB from chamber 323 into chamber 328. Additionally, it should be understood that chamber 323 may include one or more openings in addition to opening 326 and that opening 326 and any additional openings may include one or more light blocking devices to prohibit light from entering chamber 323.

Housing member 321 is generally rigid and has an approximately L-shaped profile. The shorter leg of this profile is structured as a cantilever 324 including an end wall 329 through which an electrical plug 330 extends. Plug 330 includes first prong 331 and second prong 332 with each being structured to engage with a corresponding socket of electrical wall receptacle 19. Plug 330 is typically joined to receptacle 19 with a friction fit connection that is typically aided by leaf springs biased to press against prongs 331 and 332 within receptacle 19. With this connection, terminal ends 331a, 332a of each of respective prongs 331, 332 can be inserted into the socket of receptacle 19 until end wall 329 comes into contact with an exterior portion of receptacle 19. Once fully inserted, top portions 331b, 332b engage with a corresponding surface in the socket of wall receptacle 19 to provide support for device 320. In this arrangement, as the weight of device 320 forces housing member 321 in a downward direction, as indicated by directional arrow B, top portions 331b, 332b remain in sufficient contact with the corresponding structure of the socket of wall receptacle 19 to prevent device 320 from moving out of its illustrated vertical position. Accordingly, device 320 is structured for a cantilevered connection to the receptacle 19 such that is may be suspended above the floor. As illustrated, device 320 is otherwise freestanding, with no support structure needed except for the plug 330/receptacle 19 engagement. It should be appreciated that in other embodiments, the longer leg of the L-shaped 321 housing may be arranged to articulate relative to the cantilever connection to receptacle 19 and/or housing 321 may be differently shaped.

Device 320 further includes an operating system 338 structured to control a bedbug population. System 338 includes various components disposed in both chamber 323 and chamber 328a. In the illustrated form, system 338 includes a controller 340, a fan module 342, a heat source 344, an attractant source 346, a sensor 348, and an extermination module 350. Plug 330 may be connected to controller 340 through any standard manner, like for example soldering, riveting, mechanical terminals or the like to provide an electrical power to system 338. Typically, power from an AC (alternating current) source is converted to DC (direct current) electricity to power electronic devices, and such power conversion circuitry would be included in device 320 as needed, but is not shown to preserved clarity. In still other embodiments, some or all of the components of system 338 are passive in nature, not requiring a persistent source of electrical power.

Controller 340 is comprised of one or more components that may be configured as a single unit, or distributed among two or more units. Such components may be of a solid state, electromagnetic, optical, and/or different variety as would occur to those skilled in the art. The controller 340 may include analog circuitry, digital circuitry, and/or a hybrid combination of both of these types. In one form, the controller 340 is of the programmable variety that executes algorithms and processes data in accordance with its operating logic being defined by programming instructions (such as software or firmware). Alternatively or additionally, the operating logic for controller 340 is at least partially defined by hardwired logic or other hardware. Controller 340 sends controller output signals along signal pathways 341, 343, and 345 to each of the respective fan module 342, heat source 344, and attractant source 346.

Fan module 342 may operate as a function of the controller output signal sent via signal pathway 341 and may include one or more of a motor and a fan blade assembly structured to create air flow, as would be appreciated by one having skill in the art. It should be understood that fan module 342 may be of any standard form and may include one or more components in addition to or in lieu of those mentioned. The air flow created by fan module 342 generally moves in chamber 328a past heat source 344 and attractant source 346, both of which will be discussed in further detail in general reference to FIGS. 5-7, and through openings 327, 328b and 326 to exit device 320. In one form, the air flow may carry one or more of heat from heat source 344 or an attractant from attractant source 346 to the external environment in which device 320 is placed to attract one or more insects, such as bedbugs, to device 320, as will also be explained in further detail in reference to FIGS. 5-7 generally. Furthermore, it is contemplated that the force of the air flow created by fan module 342 may be varied in different embodiments to create a stronger or weaker diffusion of heat and/or attractant. In one form, the force of the air flow may be dependent on the temperature of the heat and/or the attraction potency of the attractant. In another form for example, the force of the air flow may be dependent on the area from which a human operator desires to attract the one or more insects.

Sensor 348 is located in chamber 323 and is generally structured to detect the presence of one or more bedbugs BB in chamber 323. It should be appreciated that in alternative forms, sensor 348 may be placed external to chamber 323 on the exterior of device 320, to detect one or more bedbugs BB being attracted to device 320. Sensor 348 may include any one or more of motion detectors, heat detectors, photo-optic detectors, weight detectors, and biochemical detectors, just to name a few possibilities. In an embodiment not illustrated, it is contemplated that sensor 348 may include a closed circuit detection arrangement employing magnetic sensors. In this form, opening 326 may include a biasable door, which upon being opened in response to the weight of a bedbug, misaligns the magnetic sensors and opens the circuit to detect the bedbug's presence. In another form, sensor 348 may be structured to detect a bedbug through tarsal or spectral confirmation. Sensor 348 may additionally or alternatively include a biochemical detector to detect one or more biochemical substances indicative of bedbugs, as described above. As an alternative or additional sensing mechanism, electromagnetic radiation is used to sense bedbugs by returning, blocking, and/or dispersing the radiation in a manner that can be detected and identified as being indicative of bedbug presence, as described above with respect to devices 20, 70.

In response to detecting the presence of a bedbug, sensor 348 generates a corresponding sensor signal that is conveyed along signal path 347 to controller 340. Controller 340 may process the sensor signal and then generate an additional controller output release signal which is sent along signal pathway 349 to extermination module 350. As illustrated in phantom, extermination module 350 includes an internal reservoir 352 communicating with an applicator tip 354. A closing member 358 is biased to a closed position adjacent the applicator tip 354. The contents of reservoir 352 include an insecticide 356 toxic to bedbugs. In response to the release signal from signal pathway 349, closing member 358 opens to release insecticide 356 in a fluid form, such as an aerosol, gas, liquid, or powder into chamber 323 to exterminate the one or more bedbugs BB present therein. Closing member 358 may remain open to release the insecticide 356 into chamber 323 until controller 340 stops sending the release signal along signal pathway 349 to extermination module 350. In another form, extermination module 350 may be directly connected to sensor 348 and operate as a function of sensor 348 detecting one or more bedbugs. In this form, extermination module 350 and sensor 348 may be connected by one or more of a hard-wired or wireless electrical connection or by a mechanical connection. An insecticide toxic to bedbugs may also be present in chamber 323 either with or without extermination module 350. In one form, insecticide is present in combination with an attractant in the form of bait structured for ingestion. Furthermore, chamber 323 may also contain one or more additional attractant sources (not shown). It should be appreciated that insecticide 356 may include one or more of the varieties disclosed herein below and will generally be structured to deliver a lethal effect on a bedbug through either contact exposure to the cuticle of a bedbug, insufflation through spiracles and/or ingestion.

In an unillustrated embodiment, system 338 may further include an indicator structured to notify a human operator of a positive or negative indication of the presence of one or more bedbugs. The indicator may be linked with controller 340 and operate as a function of a controller output signal which is generated in response to the sensor signal. In one form, the indicator includes one or more visual markers in the form of a light, a light emitting diode (LED), fluorescent, incandescent, and/or neon, output amongst other possibilities. In each form, the presence of a bedbug may be indicated by, for example, a discrete yes/no indicator, a color change, a flashing sequence, or other change in indicator state. In alternative forms, the indicator provides an output indicating the presence of one or more bedbugs in the form of a colorimetric strip or an aural/audio signal. For embodiments with an indicator, such indicator may be structured to provide information in addition to a positive or negative indication of bedbug presence, such as a concentration or quantitative measurement from sensor 348.

It should be understood that device 320 may not include one or more of the components of system 338 as illustrated in FIG. 6. For example, FIG. 7 depicts an alternative embodiment as device 360 suitable for one or more of detecting, monitoring and controlling a bedbug population; where like numerals refer to like features previously described. Device 360 includes attractant source 346 in chamber 328a without a fan module or controller. In this form, plug 330 is connected to attractant source 346 as shown by electrical circuitry 361 which may include any AC/DC converters or other components desired to implement proper operation. Attractant source 346, discussed in further detail below, may include one or more attractants releasable therefrom as electrical power is supplied from plug 330 and passed therethrough. The attractant is generally structured to allure or attract one or more bedbugs to device 360.

In device 360, chamber 328a is in communication with chamber 423 of device 360 to permit passage of attractant from source 346 to chamber 423 via opening 328b. Chamber 423 opens into opening 326 and is arranged to provide a bedbug harborage like chamber 323 of device 320, with opening 328b being sized and/or shaped to prevent passage of bedbugs into chamber 328a from chamber 423. Chamber 423 includes one or more trapping features 423b disposed on each of angled surfaces 423a, with each of surfaces 423a being structured to prohibit a bedbug BB from leaving chamber 423 at opening 326. In one form, surfaces 423a may comprise one or more of a polished glass or metal or other traction reducing substance(s) designed to prohibit movement of the bedbugs across surfaces 423a. In another form, surfaces 423a may include trapping features 423b in the form of an adhesive material or petroleum jelly, with each being structured to limit bedbug movement. In still another form, surfaces 423a may be configured with one or more mechanical barriers which prohibit bedbug movement from chamber 423 in the direction of opening 326. Trapping features 423b may alternatively or additionally include a slipping, anti-friction agent that prevents sufficient traction for bedbugs to escape from chamber 423. While trapping features 423b are illustrated on surface 423a, it should be understood that one or more areas of chamber 423 may include one or more forms of trapping features 423b. It should be appreciated that a bedbug trapped in chamber 423 may remain therein until eventual extermination, removal by a human operator, or death by starvation. Additionally, device 360 may include one or more insecticides dispersed throughout chamber 423 in addition to or in lieu of trapping features 423b.

As illustrated in FIG. 7, chamber 423 further comprises bait 362 which may include one or more forms of attractant as provided by attractant source 346 and one or more forms of insecticide 356. Bait 362 may mimic a blood meal source and is generally structured to induce one or more bedbugs to enter chamber 423 and eat therefrom. When a bedbug eats bait 362, a toxic amount of insecticide 356 is ingested, resulting in extermination of the bedbug. In another embodiment, insecticide 356 may be provided in a form which is toxic to a bedbug through exposure rather than ingestion, and may be placed on or about bait 362. This form may be used in addition to or in lieu of insecticide in an ingestible form. One nonlimiting approach facilitates passing of the insecticide 356 from one bedbug to the next and/or transfer to bedbug eggs to bring about mortality.

Referring generally to FIGS. 5-7, devices 320, 360 may comprise any number of suitable materials including certain polymers, woods, metals, or any mixtures thereof. The internal surfaces of chamber 323, 423 may comprise a material the same as, or different than, the rest of devices 320, 360. For example, in one embodiment, chamber 323, 423 includes a surface suitable for the assembling of bedbugs and/or the depositing of one or more bedbug eggs thereon. In this embodiment, the surface may be a textured surface defined by fabric, paper, or wood. A surface resembling any one or more of mattress 44, box springs 45, legs 41a-41d, frame 42, headboard 43, wallpaper, carpet, plaster, and bed sheets, just to name a few possibilities, may also be included within chamber 323, 423.

In the illustrated embodiments, plug 330 of device 320, 360 is generally structured to engage with wall receptacle 19 of room 15 when wall receptacle 19 provides a 110-120 Volts AC electric power. As would be appreciated by one having skill in the art, prong 331 is slightly larger than prong 332 to provide one-way keying for engagement with receptacle 19. In an alternative form in which polarity control is not significant, prongs 331, 332 may be the same size. Plug 330 may also include a third grounding prong in addition to prongs 331, 332 in other embodiments. It is contemplated that in an alternative embodiment device 320, 360 may include an adjustable plug 330 and corresponding circuitry that can adapt to other types of power and can include an internal source, such as a battery that is charged through receptacle 19 to provide back-up power when receptacle power fails.

In varying forms, heat source 344 may use power from plug 330 to produce heat in any standard manner, including for example, with a coil resistance heater, a metal oxide resistance heater, or a PTC (Positive Temperature Coefficient) heater, just to name a few possibilities. In one instance, heat source 344 generates heat in an amount commensurate with the presence of a blood meal source and/or suitable bedbug harborage. In another form, the heat may be in an amount commensurate to release one or more attractants from attractant source 346 as described below. In one such form, heat source 344 can be structured to increase the temperature of chamber 323 to a climate most preferred by bedbugs, like for example, in the range of 70 to 120 degrees Fahrenheit. In another example, heat source 344 is structured to increase the temperature of chamber 323 to mimic the body temperature of a blood meal source to increase attraction of one or more bedbugs. In one form, where the blood meal source is a human, the temperature is raised by heat source 344 to around 98.6 degrees Fahrenheit. It should be understood that fan module 342 may push heat at any temperature out of chamber 328a through hole 327, to attract one or more bedbugs to device 320, in addition to or in lieu of modifying the temperature of chamber 323.

Alternatively or additionally, heat from source 344 can be controlled to provide a thermal level sufficient to exterminate bedbugs once present in chamber 323. In this exterminating form, heat source 344 may be used to raise the temperature of chamber 323 to a level where a sufficient duration of exposure kills a bedbug. In one exterminating form, the temperatures may be raised to somewhere in the range of 99 to 125 degrees Fahrenheit. It should be understood that in some embodiments, heat source 344 may provide even higher temperatures, where a shorter duration of exposure time is sufficient for extermination. Furthermore, heat source 344 may be coupled with one or more controls structured to dictate the time and/or temperature at which source 344 heats.

Attractant source 346 generally includes one or more attractants structure to induce one or more bedbugs into entering chamber 232, 423 of devices 320, 360. The one or more attractants may be in a gel, gas, aerosol, powder, liquid, or particulate form, just to name a few possibilities. As indicated above, one or more attractants the same as or similar to attractant source 346 may also be used on or near one or more devices 20 and 70. Attractant source 346 may include one or more holding and releasing structures dependent upon the selected attractant(s) and form in which the attractant(s) is used. For example, in one form, attractant source 346 may include a porous matrix dispensing member holding the attractant in a particulate or a powdered form. In this embodiment, the attractant may be released from attractant source 346 by the air flow produced by fan module 342 and carried out of chamber 328a or passed into chamber 323. In another form, attractant source 346 may include a gel matrix which holds the attractant. The attractant may be released from the gel matrix, for example, by exposure to heat from heat source 344 or electrical current provided by plug 330. In another form, attractant source 346 may include a holding reservoir from which the attractant may be released upon reception of a controller output signal along pathway 345. Furthermore, in another contemplated embodiment, the attractant may be time-released from attractant source 346 in a conjunction with, for example, a time delayed chemical reaction. In one such form, the chemical reaction may be dependent upon a controller output signal sent via signal pathway 345. In either of these forms, the attractant may emanate from attractant source 346 based upon its own chemical and physical properties or may be displaced from chamber 328a and/or into chamber 323 with air flow created by fan module 342.

Attractant source 346 includes one or more attractants which may be naturally occurring or synthetic bedbug alluring compounds structured to mimic one or more biological or physical requirements essential for bedbug survival. In one form, the attractant may include any combination of one or more of avian or mammalian pheromones, hormones, sweat, epidermic oils, blood, choline, and other body odors, such as those associated with, for example, halitosis. The bedbug attraction associated with any combination of compositions in attractant source 346 may be further enhanced by the production of heat by heat source 344. Furthermore, heat can be used to liberate attractant with or without the aid of a fan. Attractant source 346 may further be placed within a controlled atmosphere or emit one or more gases therefrom by evaporation, sublimation, diffusion, or such other mechanism as would occur to those skilled in the art.

In one embodiment, attractant source 346 provides a controlled level of carbon dioxide ($CO_2$) in and/or surrounding device 320, 360 to attract bedbugs. For instance, the $CO_2$ level can be regulated to simulate the concentration of $CO_2$ exhaled by a blood meal source for a bedbug. Accordingly, this level may mimic that of a mammal, including but not limited to, domesticated animals and pets, bats, rats, or humans. In one preferred form, a $CO_2$ level indicative of a human blood meal source is provided, such as a $CO_2$ level between about 0.01 and 1.0 percent of the atmosphere in or surrounding device 320, 360. In another preferred form, attractant source 346 may distribute between 0.003 to 0.042 mL of $CO_2$ per square meter of surface of either attractant source 346 or device 320, 360. Device 320, 360 may include an internal reservoir of $CO_2$ and one or more release mechanisms to control the distribution rate of the $CO_2$. In alternative embodiments, the humidity levels of the atmosphere in or surrounding device 320, 360 may be altered in addition to or in lieu of a $CO_2$ level change.

In an embodiment where attractant source 346 includes a sweat simulating compound, various levels of sodium chloride (NaCl) and urea $((NH_2)_2CO)$ may be included. One or more odorants, such as 2-methylphenol or 4-methylphenol, may be included in attractant source 346 with or without the presence of one or more of sodium chloride or urea. In one form, the epidermic oil may mimic sebum as produced by the human sebaceous gland and may include a mixture of one or more of wax monoesters, triglycerides, free fatty acids, and squalene. It should be understood that the quantity of each may vary in order to control one or more chemical characteristics of the epidermic oil, such as for example, stereochemistry, pH level, or electrochemistry, to assist in its attracting function. It is further contemplated that attractant source 346 may include additional compounds associated with the human body, including glucose, lactic acid, or bile salts such as choline, just to name a few example. Furthermore, one or more of sodium taurocholate and sodium glycocholate or a mixture thereof may be added to the various forms and embodiments of attractants included in attractant source 346.

In another form, attractant source 346 may include one or more attractants associated with bedbugs. By way of non-limiting example, pheromones may be included in one or more forms of an assembling or aggregative pheromone, a sexual pheromone, or an aggression stimulating pheromone. In one example, the pheromone is similar to one contained in one or more scent producing glands of a bedbug. In another example, one or more extracts of bedbug excreta or other bedbug secretions may be used. In yet another example, an extract of excreta obtained using a mixture of water and methanol solvent is present as an attractant.

It should be appreciated that bait 362 may include any whole or part of a blood meal source, including but not limited to synthetic or natural avian or mammalian blood. While illustrated in connection with device 360, and described in connection with both of devices 320, 360, it should be appreciated that bait 362 may be implemented with either of the other devices 20 and 70. For one implementation, the mammalian blood may be in the form of human blood and may include one or more of red blood cells, white blood cells, platelets, and plasma, the plasma including but not limited to, albumin, thrombogenic factors, immunoglobulins, hormones, proteins, and/or electrolytes. It should be understood that the mixture of the above elements may change in alternative embodiments to alter attracting or ingestion qualities. It is contemplated that the bait 362 may be placed in or about chamber 323, 423 or on or about the exterior of each of the respective devices 320, 360. In one form, the bait may be intermixed with one or more forms of attractant releasable by attractant source 346 as described above. In another form, bait 362 is mixed with insecticide 56 such that consuming the bait will deliver a lethal dose of insecticide 356 to a bedbug, as described above in regard to FIG. 7.

In one unillustrated form, in which bait 362 is utilized, it may include one or more features designed to simulate a human being. For example, an external layer mimicking skin may enclose an internal reservoir including one or more blood meal forms, which in one embodiment may be human blood. The external layer may include one or more of the above listed attractants and may further include additional features, such as pores, hair follicles, and/or hair shafts. In one particular implementation, the external layer is indicative of the arms and shoulder of a human blood meal. The bait 362 may further emit $CO_2$ and or be placed in a $CO_2$ controlled environment as previously described. Heat from heating source 344 may further be included to make the temperature of the external layer indicative of the epidermis of a human. One or more forms of insecticide may be mixed with a blood meal attractant and structured so that as a bedbug pierces the external layer and attempts to feed on the blood meal, a lethal dosage of insecticide is delivered to the bedbug. The bait 362 may further include one or more features capable of restricting blood loss from the reservoir from piercings created by a bedbug.

It should be further understood that the components of devices 320, 360 can be connected using wired or wireless techniques. For a further embodiment, information is relayed by a wired or wireless communication signal pathway from device 320, 360 to a remote site for further data collection and analysis. This remote site could be a computer coupled to device 320 and/or 360 by a computer network in a designated room of a hotel, nursing home, cruise ship, train, dormitory, barracks, hospital, or the like and/or could even be remote relative to such structures, like a pest control service provider business location or the like. In still other arrangements, it should be appreciated that one or components of system 338 may be integral to each other such that they are represented as separate features in only a logical sense. It should be appreciated that devices 320 or 360 could be adapted to provide an air freshener or fragrance and/or to provide air purification in addition to insect control operations.

Figure 8:
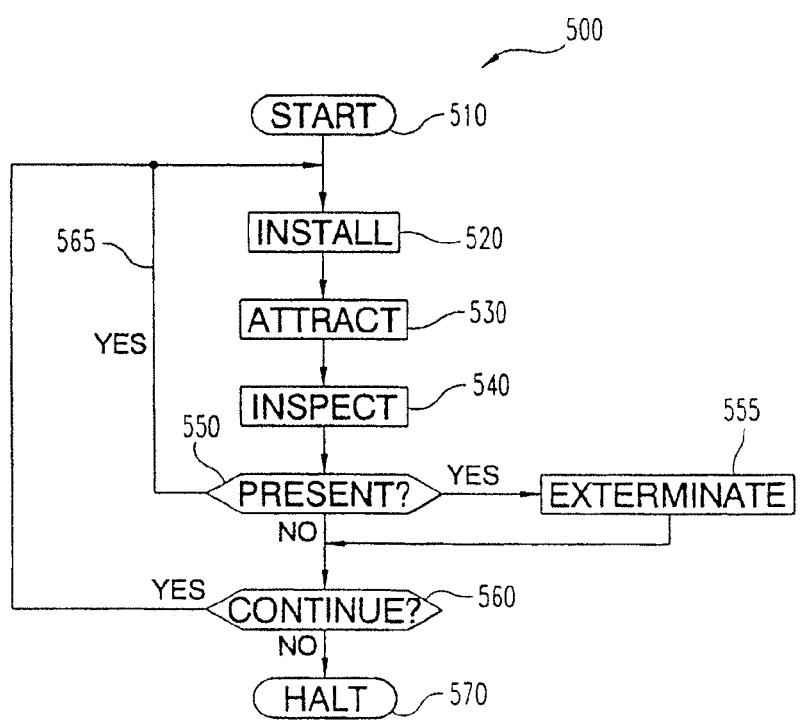
FIG. 8 is a flowchart depicting one procedure for using the system of FIG. 5.

FIG. 8 depicts one procedure 500 for using system 310 in flowchart form. At stage 510, procedure 500 begins. Following stage 510 is stage 520 in which system 310 is installed, including for example engaging device 320, 360 or one or more variations thereof with wall receptacle 19 of room 15. After installation, system 310 begins to attract one or more bedbugs in accordance with one or more embodiments disclosed. At stage 540, inspection of system 310 occurs to see if bedbugs or signs indicative of bedbug infestation are present. It is contemplated that the inspection may be facilitated by one or more of sensor 348 or visual inspection by a human operator. A determination of the presence of one or more bedbugs is made at stage 550. If it is determined that one or more bedbugs are present, the bedbugs may be exterminated at stage 555. In one form, extermination module 350 exterminates the bedbugs in response to an output signal from controller 340. In another form, where extermination module 350 is absent, the human operator may determine whether to exterminate the bedbugs. If no bedbugs or signs indicative of bedbugs are present and a sufficient period of time has passed to satisfy the human operator that no bedbugs are present, then the operator may proceed to step 570 and halt procedure 500. If however signs of bedbugs are present or a sufficient period of time has not passed to satisfy the human operator of a lack of presence of bedbugs, procedure 500 may be started over again as indicated by arrow 565. Procedure 500 may be continually repeated until an entire bedbug population has been removed and/or the human operator is satisfied that a sufficient period of time has passed without any indication of bedbug presence, indicating their absence.

As indicated above, it is contemplated that one or more embodiments may include an insecticide 124, 356 effective for exterminating one or more bedbugs. In one form, insecticide 124, 356 may include one or more of 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl ODD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfl uthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram (XDE-175), spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

It is also contemplated that various embodiments of the present application can also be used with herbicides and fungicides, both for reasons of economy and synergy. Additionally or alternatively, one or more embodiments of the application can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy and synergy. For more information consult "Compendium of Pesticide Common Names" located at http://www.alanwood.net/pesticides/index.html as of the filing date of this application. Also consult "The Pesticide Manual" 14th Edition, edited by CDS Tomlin, copyright 2006 by British Crop Production Council.

Various embodiments of the present application can be used with other compounds to form synergistic mixtures where the mode of action of the compounds in the mixtures is the same, similar, or different. Examples of mode of actions include, but are not limited to: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with one or more embodiments of the present application: piperonyl butoxide, piprotal, propyl isome, sesamex, sesamolin, and sulfoxide.

Many different embodiments of the present application are envisioned. In one example, a device is structured to detect one or more biochemicals indicative of one or more insect species in lieu of or in addition to one or more bedbug species. Additionally or alternatively, insecticides and other extermination techniques can be adapted to eliminate attracted insects other than bedbugs. Such alternative insect species can include other pestiferous insects such as lice, Rhodnius, and/or mosquitoes.

In another example, one embodiment comprises operating a device to determine if bedbugs are present in a room, including: analyzing a substance from the room to detect a biochemical indicative of biochemistry selective to bedbugs in the indoor space; and if the biochemical is detected by analyzing of the substance then indicating the bedbugs are present to a human operator. The operating of the device may include one or more of applying an aerosol, performing a wipe assay, and obtaining an air sample.

Another example includes an apparatus comprising: a sensing arrangement including one or more sensors structured to analyze a substance received by the device and generate one or more corresponding sensor signals; a controller operatively coupled to the sensing arrangement, the controller being structured with operating logic to determine if nitrophorin is included in the substance based on the one or more corresponding sensor signals and generate an output signal representative of the presence of bedbugs in response to a presence of the nitrophorin in the substance; and an output device responsive to the output signal to operate in accordance with the bedbug presence. The apparatus may further include means for exterminating insects that is responsive to the output signal. In one form directed to bedbugs, the exterminating means includes at least one insecticide.

An additional embodiment includes selecting a room to evaluate for presence of bedbugs; receiving a substance from the room; detecting a presence of nitrophorin in the substance; and in response to the presence of nitrophorin, activating a device indicative of the presence of bedbugs.

Still, another embodiment is directed to a method for determining the presence of bedbugs in a room, including: obtaining a sample of a substance from the room; analyzing the sample to determine if nitrophorin is present in the substance; and providing an indication of the presence of bedbugs in response to the determination of the presence of nitrophorin.

A further embodiment comprises a plug-in device that includes a housing defining an insect harboring chamber, an electric-powered device disposed relative to the chamber to attract insects, and a plug member electrically coupled to the electric-powered device. The plug is structured to engage an electric socket and defines a cantilever to support the plug-in device above floor level when engaged in the electric wall socket.

Another embodiment of the present application includes: providing an insect trap with a chamber for insect harborage, attracting insects of one or more species to the chamber by providing one or more indications of a blood meal source for such insects at the trap, and at least one of detecting the insects in the trap and providing an insecticide toxic to the insects in the trap. In one form the insects include bedbugs.

Yet another embodiment comprises a device including a chamber structured to harbor insects of one or more species and an insect attractant disposed relative to the chamber to attract insects thereto. The attractant provides one or more indications corresponding to a blood meal source for the insects. The insect attractant is disposed relative to the chamber to attract the insects to the chamber to expose the insects to an insecticide toxic to the insects in the chamber. In one form, the one or more species of insects targeted by the device include bedbugs.

Still another embodiment comprises a device that includes a chamber structured to harbor insects and an insect attractant disposed relative to the chamber to attract insects thereto. The insect attractant is indicative of an insect blood meal source, and includes one or more of: (a) a heat output corresponding to the insect blood meal source, (b) one or more sweat constituents corresponding to the insect blood meal source, and (c) a carbon dioxide concentration corresponding to the insect blood meal source. In one form, the insect attractant targets bedbugs.

A further example includes: providing an insect trap with a chamber for insect harborage, attracting insects to the chamber by providing one or more indications of a blood meal source at the trap, and at least one of detecting the insects in the trap and providing an insecticide toxic to the insects in the trap. One more specific, nonlimiting form includes cantilevering the trap above floor level by engaging a plug member of the trap into an electrical outlet and/or targeting bedbugs with the trap.

In another example, a bedbug trap defines a chamber for bedbug harborage, and includes: means for attracting bedbugs to the chamber by providing one or more indications of a blood meal source at the trap, and at least one of means for detecting the bedbugs in the trap and means for providing an insecticide toxic to the bedbugs in the trap. One more specific, nonlimiting arrangement additionally includes means for cantilevering the bedbug trap above floor level by engaging a plug member of the trap into an electrical outlet.

Still another example of a further embodiment of the present application comprises a device with a chamber structured to harbor bedbugs and a bedbug attractant disposed relative to the chamber to attract bedbugs thereto. The bedbug attractant provides one or more indications to bedbugs corresponding to a bedbug blood meal source. The bedbug attractant is disposed relative to the chamber to attract the bedbugs to the chamber to expose the bedbugs to an insecticide toxic to the bedbugs in the chamber.

In yet another example, a device defines a chamber structured to harbor bedbugs and includes a bedbug attractant disposed relative to the chamber to attract bedbugs thereto. The bedbug attractant is indicative of a bedbug blood meal source, and includes one or more of: (a) a heat output corresponding to the bedbug blood meal source, (b) one or more sweat constituents corresponding to the bedbug blood meal source, and (c) a carbon dioxide concentration corresponding to the bedbug blood meal source. In one form, the device further includes an insecticide to exterminate bedbugs in the chamber.

A further example comprises a plug-in device that includes a housing defining an insect harboring chamber, an electric-powered device disposed relative to the chamber to attract insects, and a plug member electrically coupled to the electric-powered device. The plug is structured to engage an electric socket and defines a cantilever to support the plug-in device above floor level when engaged in the electric wall socket. The device may be further structured to trap or exterminate insects in the chamber.

Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. An insect control device, comprising:
    a housing member including an exterior wall, the housing member defining an internal chamber, and
    a sensing arrangement positioned in the internal chamber of the housing member, the sensing arrangement including:
    one or more sensors configured to analyze a substance received by the sensing arrangement and generate a sensor signal,
    a controller electrically connected to the one or more sensors and configured to receive the sensor signal, the controller is further configured to determine if the substance is indicative of the presence of one or more insects, and
    a power source electrically connected to the controller and configured to provide power to the one or more sensors and the controller,
        wherein the exterior wall of the housing member includes one or more sensor openings, and each of the one or more sensors include a sensing portion positioned outside the internal chamber of the housing member and configured to be exposed to an environment external to the internal chamber, wherein each of the one or more sensors extends from the sensing portion, through one of the one or more sensor openings, and into the internal chamber.
2. The insect control device of claim 1, wherein the housing member includes a top cover configured to enclose the internal chamber.
3. The insect control device of claim 1, wherein the housing member is configured to attach to a leg of a bed.
4. The insect control device of claim 1, wherein the sensing arrangement further includes an indicator electrically connected to the controller and configured to provide an output to a user of the insect control device in response to the controller determining that one or more insects are present.
5. The insect control device of claim 4, wherein the indicator produces a visual output using one or more light sources in response to the controller determining that one or more insects are present.
6. The insect control device of claim 1, wherein the power source comprises one or more batteries configured to provide electrical power to the sensing arrangement.
7. The insect control device of claim 1, wherein the sensing arrangement further includes an extermination module positioned in the internal chamber of the housing member and being electrically connected to the controller, wherein the extermination module is configured to exterminate one or more insects in response to the controller determining that one or more insects are present.
8. An insect control device, comprising:
    a housing member including an exterior wall, the housing member defining an internal chamber, and
    a sensing arrangement positioned in the internal chamber of the housing member, the sensing arrangement including:
    one or more sensors configured to analyze a substance received by the sensing arrangement and generate a sensor signal,
    a controller electrically connected to the one or more sensors and configured to receive the sensor signal, the controller is further configured to determine if the substance is indicative of the presence of one or more insects, and
    a power source electrically connected to the controller and configured to provide power to the one or more sensors and the controller,
    wherein the sensing arrangement further includes an extermination module positioned in the internal chamber of the housing member and being electrically connected to the controller, wherein the extermination module is configured to exterminate one or more insects in response to the controller determining that one or more insects are present, and
    wherein the extermination module includes:
    a reservoir configured to hold insecticide configured to exterminate one or more insects, and
    an applicator tip configured to deliver the insecticide to the one or more insects.
9. The insect control device of claim 8, wherein:
    the exterior wall includes an extermination module opening, and
    the applicator tip of the extermination module is positioned outside the internal chamber of the housing member, wherein the extermination module extends from the applicator tip, through the extermination module opening, and into the internal chamber of the housing member.
10. The insect control device of claim 7, wherein a user interface is positioned in the internal chamber and is electrically connected to the extermination module, wherein the user interface is configured to cause the extermination module to release an insecticide in response to a user interacting with the user interface.

11. The insect control device of claim 1, wherein the housing member includes a handle structured for engagement by a hand of a user.

12. A method of controlling insects, the method comprising:
- receiving, by a sensor, a substance from an environment,
- generating, by the sensor and in response to receiving the substance, a sensor signal,
- generating, by a controller and in response to receiving the sensor signal, an output signal indicating that the substance is indicative of the presence of one or more insects, and
- outputting, by an output device and in response to receiving the output signal, an indication that the substance is indicative of the presence of one or more insects,
- wherein outputting the indication comprises outputting, by an extermination module, an insecticide configured to exterminate one or more insects.

13. The method of claim 12, further comprising:
- determining, by the controller and in response to receiving the sensor signal, whether the substance is indicative of the presence of one or more insects, and
- generating, by the controller, the output signal indicating that one or more insects are present.

14. The method of claim 12, wherein outputting the indication comprises outputting, by an indicator, a visual output by one or more light sources indicating the presence of one or more insects.

15. The method of claim 12, wherein outputting the indication comprises:
- outputting, by an indicator, a visual output by one or more light sources indicating the presence of one or more insects.

* * * * *